US008999263B2

(12) United States Patent
Peterman et al.

(10) Patent No.: US 8,999,263 B2
(45) Date of Patent: Apr. 7, 2015

(54) MICROFLUIDIC SEPARATION DEVICE

(71) Applicant: OndaVia, Inc., Hayward, CA (US)

(72) Inventors: Mark C. Peterman, Fremont, CA (US); Merwan Benhabib, San Francisco, CA (US); Benjamin A. Obrock, San Francisco, CA (US)

(73) Assignee: OndaVia, Inc., Hayward, CA (US)

( * ) Notice: Subject to any disclaimer, the term of this patent is extended or adjusted under 35 U.S.C. 154(b) by 261 days.

(21) Appl. No.: 13/796,939

(22) Filed: Mar. 12, 2013

(65) Prior Publication Data
US 2013/0266479 A1 Oct. 10, 2013

Related U.S. Application Data

(63) Continuation-in-part of application No. 12/455,256, filed on May 29, 2009, now Pat. No. 8,414,755.

(51) Int. Cl.
G01N 21/65 (2006.01)
B01L 3/00 (2006.01)
B01D 57/02 (2006.01)
B01D 61/42 (2006.01)

(52) U.S. Cl.
CPC ........ G01N 21/658 (2013.01); B01L 3/502761 (2013.01); B01D 57/02 (2013.01); B01D 61/427 (2013.01)

(58) Field of Classification Search
CPC ........................ B01L 3/502761; G01N 21/658
See application file for complete search history.

(56) References Cited

U.S. PATENT DOCUMENTS

2004/0035701 A1* 2/2004 Han et al. ................ 204/451
2009/0214392 A1* 8/2009 Kameoka et al. ......... 422/102

OTHER PUBLICATIONS

Wang et al. An optofluidic device for surface enhanced Raman spectroscopy, 2007, Lab on a Chip, vol. 7, pp. 630-632.*

* cited by examiner

Primary Examiner — Melanie Y Brown
(74) Attorney, Agent, or Firm — Lumen Patent Firm

(57) ABSTRACT

A microfluidic separation device is provided that includes a first sample channel region and a second sample channel region, where the first sample channel region has an array of channels that are smaller than the second channel region, a first detection region and a second detection region located at the interface of the first sample channel region, a detection channel, an illuminating electric field, Raman-scattering nanoparticles having surface plasmon resonances for detection when illuminated by the electric field, where the resonances create an enhanced local electric field along specific directions resulting in an enhanced Raman response, and a nanoparticle input channel disposed to input the nanoparticles into the second sample channel region, where the nanoparticles are larger than the cross-section of the first sample channel region and the cross-section of the second detection region, where the nanoparticles collect in the first detection region to form region of densely packed nanoparticles.

9 Claims, 10 Drawing Sheets (a)

(b)

*(d)*

MICROFLUIDIC SEPARATION DEVICE

CROSS-REFERENCE TO RELATED APPLICATIONS

This application is continuation-in-part of U.S. patent application Ser. No. 12/455,256 filed May 29, 2009, now U.S. Pat. No. 8,414,755 which is incorporated herein by reference.

FIELD OF THE INVENTION

The invention relates generally microfluid separation devices. More particularly, the invention relates to a microfluid separation device having narrow channels to trap signal-enhanced particles at a detection region within a longer separation channel.

BACKGROUND

The residential drinking water for forty-one million Americans in twenty-four major metropolitan areas contains pharmaceutical compounds. The human health effects of long-term, chronic exposure to trace levels of these hormones, endocrine-disrupting compounds, painkillers, and antibiotics are not yet fully understood, although the impact on aquatic life has been observed as changes in reproductive health and function. The importance of this potential threat to human health is the subject of much recent research and investigation highlighted by two late-2008 conferences sponsored by the National Institute of Environmental Health Sciences regarding pharmaceuticals and personal care products in the environment.

These compounds are present at minute, yet potentially significant, concentrations. Existing tools that can measure these very low concentrations—e.g., liquid chromatography with mass spectroscopy (LC-MS)—are expensive, complex, laboratory-based instruments. Current portable monitoring tools cannot even approach measuring parts per billion, let alone the parts-per-trillion levels of pharmaceuticals found in drinking water. At the same time, our water sources are threatened by numerous other pollutants with regulatory limits at the parts-per-billion level: agricultural run-off, heavy metals, military remnants, and industrial waste. The ability to monitor our water supply at the parts-per-billion level at the source or in the field would vastly improve the capabilities of water suppliers. This ability will in turn allow water suppliers to increase monitoring frequency, to implement remediation steps, and to focus research efforts on understanding of the health effects of chronic exposure.

Laboratory detection equipment such as embedded surface-enhanced Raman spectroscopy (eSERS) can address this deficiency by measuring compounds in aqueous solution at better than one part per billion. This embedded detection approach relies upon geometric constraints within a microfluidic channel to trap gold nanoparticles, creating a region of extreme nanoparticle density—i.e., maximum surface area in a minimum volume—required for the eleven to fifteen order-of-magnitude enhancement of Raman signal.

The presence of pharmaceuticals in the environment has been documented since the 1980s. Recent surveillance studies have brought this concern to the forefront, highlighting the widespread impact upon the US population. It has been reported that at least 41 million Americans across 24 major metropolitan areas have detectable levels of pharmaceuticals in their drinking water. Multiple US Geological Survey studies and reports since the late 90's have demonstrated the presence of contaminants in ground and surface water. Moreover, the NIEHS sponsored two late-2008 conferences regarding pharmaceuticals and personal care products in the environment, the US EPA launched Information Collection Request for health care facilities regarding unused pharmaceuticals, and the National Academy of Sciences had a December 2008 workshop on screening risk from pharmaceuticals in drinking water.

The health effects of these trace compounds on humans are not well understood, although reports regarding the impact on non-target species are widely known. Many fish experience reproductive problems, with male fish producing female proteins and female fish growing male reproductive organs. In some locations downstream from wastewater treatment facilities, the ratio of males to females is wildly skewed, even though the populations are normal upstream.

The challenge with understanding the health effect on humans is the time-scale at which an effect might occur and the wide range of potential contaminants at minute concentrations over a large area. A recent study found 34 pharmaceuticals and other organic wastewater contaminants in a New Jersey stream downstream from a wastewater-treatment facility. These chemicals included antibiotics (triclosan and sulfamethoxazole), nicotine metabolites (cotinine), decongestants (diphenhydramine), and analgesics (acetaminophen). Philadelphia discovered 56 pharmaceuticals and by-products in treated drinking water, including epilepsy and mental illness medications in the tens of parts per trillion range.

Pharmaceuticals are not the only contaminant of concern in drinking water; the total number of potential contaminants is staggering. Industrial waste and agricultural run-off are both frequently detected in surface water, with levels regulated by the EPA. Some compounds are widely used in industrial or agricultural settings, such as atrazine to control broadleaf weeds—which has been reported to cause reproductive problems in non-target species (including humans). Some compounds may be intentionally added to food or water, such as the addition of melamine to infant formula—a chemical that has been added nefariously to Chinese products and inadvertently to American products. Other compounds leach from storage containers, such as bisphenol A (BPA) from plastic bottles. A portable instrument that could measure these compounds at the part-per-billion level would be valuable to water suppliers, regulators, and consumers world-wide to maintain safe supplies, increase monitoring frequency and accuracy, and provide comfort that our water is safe to drink.

The first line of defense for protecting the water supply—and ultimately, human health—from pharmaceuticals and other contaminants is tools to rapidly and accurately measure trace levels of compounds in the field or at the source. Unfortunately, water analysis at the required accuracy with a portable instrument is currently not possible. Current portable instruments either measure overall water quality or measure water constituents. Tools that measure water quality focus on pH, turbidity, and total dissolved solids to provide a generic measure of water cleanliness. These tools are valuable for the speed at which they provide confidence, but do not measure actual water contaminants. Tools that measure water constituents primarily focus on UV/vis spectrometry or colorimetry. Both analytical methods are limited to measuring parts per million, far from the regulatory limits of many compounds, and even farther from the concentration of pharmaceuticals in drinking water.

Not only are the total number of potential contaminants staggering, but so are also the number of required analytical techniques. Analysis of specific analytes at minute levels within a water sample requires complex, expensive laboratory equipment. A variety of laboratory techniques exist, with the EPA providing a list of available and approved techniques for compounds of concern. The American Public Health Association, American Water Works Association, and Water Environmental Federation publish "Standard Methods for the Examination of Water and Wastewater", an extensive treatise on water analysis methodology. Most analytes require a two-step technique: chemical separation followed by analytical spectroscopy. This two-step approach is essential when a mixture is considered. The combination of signals from multiple analytes will wash out the signal from any individual compound. Consequently, field samples are frequently sent to a laboratory for chromatographic separation followed by some form of analytical detection.

Separation is critical for reliable, accurate detection. But, without adequate detection techniques, separations are of little value. A variety of methods are used in water analysis. Ultraviolet-visible (UV/vis) spectroscopy is popular, as the technique is simple and quantitative. However, UV/vis cannot detect material concentrations much better than one part per million, limiting its value to high-level screening of basic ions or gross contaminants. Other optical methods such as fluorescence, refractive index measurements, or colorimetry either require specialized chromaphores or similarly lack sensitivity.

Mass spectrometry (MS) is a widely used and popular approach with the ability to measure at the required sensitivities. MS is a standard add-on to liquid chromatography systems (LC-MS), although at a cost of tens of thousands of dollars. MS requires ionization of the analyte of interest, breaking the compound into various subcomponents. These charged components pass through a magnetic field and are differentially deflected onto a detector array. The distribution across the detector array is a function of the charge-to-mass ratio. Various derivatives that are more sensitive or more accurate have been developed, but it is possible to detect sub-ppb using MS. On the other hand, the disadvantages of MS are 1) high cost, and 2) the impracticality of developing a portable, handheld system. These limitations keep MS as a laboratory instrument for trained operators.

What is needed is a portable, rapid measurement analysis instrument to allow water suppliers to 1) determine more quickly which compounds are present, 2) choose remediation steps, 3) add specific monitoring of ground and surface water, 4) increase studies of the human health effects of specific pharmaceuticals, and 5) eliminate the source through targeted public educating on proper disposal of prescription and non-prescription drugs.

SUMMARY OF THE INVENTION

The present invention provides a microfluidic separation device that includes a first sample channel region and a second sample channel region, where the first sample channel region has an array of channels that are smaller than the second channel region, a first detection region and a second detection region located at a planar interface of the first sample channel region, a detection channel, an illuminating electric field, Raman-scattering nanoparticles, where the Raman-scattering nanoparticles have surface plasmon resonances for detection when illuminated by the illuminating electric field, where the surface plasmon resonances create an enhanced local electric field along specific directions, where the enhanced local electric field results in an enhanced Raman response, and a Raman-scattering nanoparticle input channel disposed to input the Raman-scattering nanoparticles into the second sample channel region, where the Raman-scattering nanoparticles are larger than the cross-section of the first sample channel region and larger than the cross-section of the second detection region, where the Raman-scattering nanoparticles are disposed to collect in the first detection region to form region of densely packed the Raman-scattering nanoparticles.

According to one aspect, the invention further includes a Raman-scattering nanoparticle output channel, where the Raman-scattering nanoparticle input channel and the Raman-scattering output are disposed opposite the densely packed Raman-scattering nanoparticles along the second sample channel region, where the nanoparticle input channel is disposed at a proximal side of the densely packed Raman-scattering nanoparticles and the Raman-scattering nanoparticle output channel is disposed at a distal side of the densely packed Raman-scattering nanoparticles.

According to another aspect, the invention further includes the first Raman-scattering nanoparticle input channel and a second the Raman-scattering nanoparticle input channel, where the first and the second Raman-scattering nanoparticle input channels are disposed proximal to and parallel each other.

In yet another aspect, the invention further includes a Raman-scattering nanoparticle output channel, the first Raman-scattering nanoparticle input channel and a second the Raman-scattering nanoparticle input channel, where the first and the second Raman-scattering nanoparticle input channels disposed proximal to and parallel with each other, where the second Raman-scattering nanoparticle input channel and the Raman-scattering output channel are disposed opposite the densely packed Raman-scattering nanoparticles along the second sample channel region, where the nanoparticle input channel is disposed at a proximal side of the densely packed Raman-scattering nanoparticles and the Raman-scattering nanoparticle output channel is disposed at a distal side of the densely packed Raman-scattering nanoparticles.

According to another aspect of the invention, a first detection region and a second the detection region are dispose on opposite sides of the detection channel, where a first the sample channel is connected to the first detection region and a second the sample channel is connected to the second detection region, where the first sample channel is parallel with the second sample channel.

In a further aspect of the invention, a first sample channel is connected to a proximal side of the detection region and a second sample channel is connected a distal side of the detection region, where the densely packed Raman-scattering nanoparticles are disposed on opposite sides of the detection region.

According to another aspect of the invention, a first sample channel having a first Raman-scattering loading channel is connected to a proximal side of the detection region and a second sample channel having a second Raman-scattering loading channel is connected a distal side of the detection region, where the densely packed Raman-scattering nanoparticles are disposed on opposite sides of the detection region.

In another aspect of the invention, the sample channel includes a first constricted region and a second constricted region disposed on opposite sides of the detection region.

According to another aspect of the invention, a first detection region is disposed on a first side of the sample channel and a second detection region is disposed on a second side of the sample channel, where the first and the second detection regions are opposite of each other across the sample channel.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The current invention provides a microfluidic separation device that is useful for surface-enhanced Raman spectroscopy (SERS) and other detection methods. Raman spectroscopy in general provides a chemical signature for a compound, but the Raman signal is generally too weak for part-per-billion detection levels. However, when a metallic nanoparticle that is smaller than the wavelength of light is introduced into the sample, the illuminating electric field will create surface plasmon resonances if there are free electrons in the nanoparticle, where the nanoparticle can be gold, silver, or copper beads, for example. These oscillating charges create an enhanced local electric field along certain directions. This field results in a much stronger Raman response. SERS experiments are often characterized by "hot spot" regions. Here the SERS signal reaches single-molecule detection capabilities. These regions are most likely due to nanoparticle alignments that create even larger electric field enhancements.

Using SERS for analyte detection has been under study. It is believed the large signal enhancement creates new opportunities to measure very small concentrations: picomolar, femtomolar, and potentially even single molecules. The challenge with SERS is creating an interaction between the analyte and the metal surface. The highest-sensitivity studies rely upon binding events to bring the molecules into close contact. While very sensitive, this approach is limited to measuring a previously decided set of analytes for which the nanoparticles are prepared. The binding does not need to be specific; for example, treatments with octadecylthiol have been used successfully for SERS on planar substrates.

Figure 1:
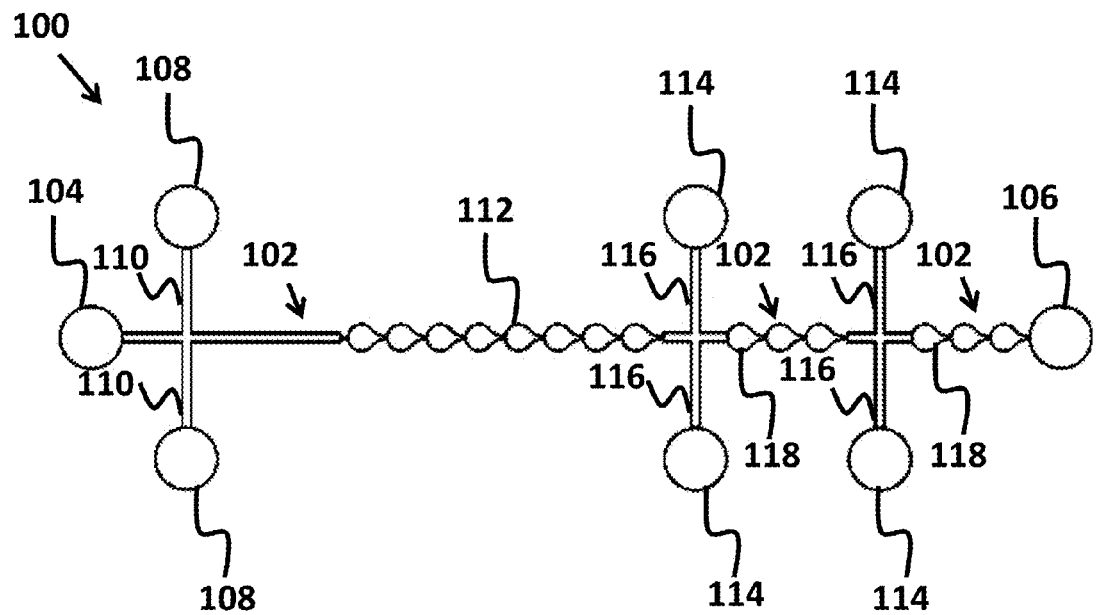
FIG. 1 shows a top view of one embodiment of the microfluidic device according to the present invention.

According to one aspect or the current invention, a sensitive detection system incorporated in a portable device is provided. The invention includes packing sections along a microfluidic separation channel with nanoparticles, for example gold nanoparticles, at a high density. The invention creates many hot spots simply through particle density. The invention uses microfluidic delivery and narrow channel geometries to trap signal-enhancing particles at a detection location within a longer separation channel. Referring now to the figures, FIG. 1 shows a top view schematic of a microfluidic separation device 100 having a main channel 102 spanning from a fluid input 104 to a fluid output 106. The microfluid separation device 100 includes at least one sample loading port 108 connected to the main channel 102 by a sample loading channel 110. Separation regions 112 are disposed down stream from the sample loading channel 110. The invention further includes at least one detection particle loading port 114 connected to the main channel 102 by a detection particle channel 116. At least one detection region 118 is disposed down stream from the detection particle channel 116. As shown in the exemplary device of FIG. 1, the main channel 102 is intersected by two perpendicular sample loading channels 110 to load the sample under study into the main channel 102, while the detection particle channel 116 is for loading the nanoparticle markers into the main channel 102.

Figure 2:
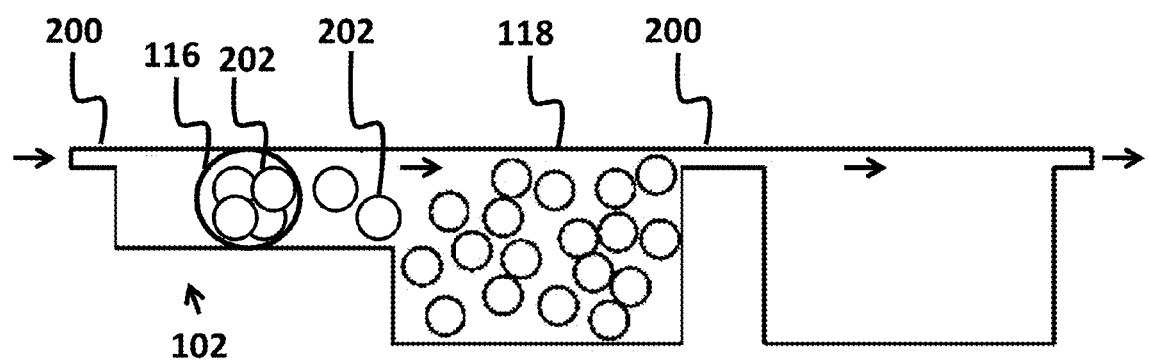
FIG. 2 shows a side cutaway view of a detection region of the microfluidic device in FIG. 1 according to the present invention.

FIG. 2 shows a side view of a detection region 118 of the microfluidic mixing device 100 in FIG. 1 according to the present invention. Proximal to the intersection of the detection particle channels 116 and the main channel 102 are geometric constrictions 200 that trap the nanoparticles 202 within the detection region 118. Further shown are arrows to indicate the flow direction of the fluid within the microfluid separation device 100. The fluid moves the nanoparticles 202 along the flow path to compact them within the detection region 118. The current invention relies purely on proximity by creating a region densely packed nanoparticles 202. According to one exemplary structure of the invention, tight packing density (close-packed spacing) predicts a maximum volume ratio of 74% spherical nanoparticles for a microfluidic channel region 118 that is 50 µm in length and has a 25 µm width and depth, loaded with 40-nm gold nanoparticles 202, this type of volume packing will have a surface area nearly 700 times greater than the surface area of the channel region. Furthermore, the narrow regions between nanoparticles 202 with the non-linear path through the matrix will increase interactions. The current invention provides a sensitivity requirement of detecting materials in parts per billion.

In the base configuration of the current invention, included is a main channel 102 with at least one crossing sample loading channel 110 and at least one nanoparticle loading channel 116, and the detection region 118. The detection region 118 has geometric constraints 200 that prevent particles 202 of a certain size from entering the main channel 102 in either direction, or from continuing past the detection channel 118. The nanoparticles 202 may be metallic, such as gold, copper, silver, fluorescent particles, magnetic particles, particles having binding chemistry, latex particle, polystyrene particles or quantum dots for surface-enhanced Raman scattering. According to one aspect, the particles are on the order of 10 nm to 10 μm. The particles 202 may also be fluorescent beads designed to bind with an analyte of interest for an ELISA-type signaling approach. These particles can be loaded using any type of fluid driving mechanism such as electroosmosis, electrophoresis, fluid pressure, moveable wall pressure, undulary electroosmosis, undulary electrophoresis, undulary fluid pressure or undulary moveable wall pressure. Note that between the sample input channel 110 and detection region 118 can be a separation region 112 that isolates individual compounds (undulary electroosmosis, electrophoresis, or chromatography) before entering the detection region 118.

It should be apparent there are many geometries may be used to create these detection regions 118. The constrictions 200 can occur in the vertical direction, reducing the detection region 118 size from top to bottom. This approach requires etching short depths or sacrificial layers. The constrictions 200 can also occur in the horizontal direction, which would rely upon lithographic abilities to define the narrowest gaps.

According to one aspect of the invention, the Raman signal can be further increased by using chemistries, both nonspecific and specific, to bind analytes to the nanoparticles 202. With over a billion nanoparticles 202 in each detection region 118, along with multiple detection regions 118, a separation column 102 could hold a large number of modified nanoparticles 202. For example, with five detection regions 118, each holding two hundred different bindings, this system 100 could detect one thousand compounds while maintaining greater than five million nanoparticles 202 per region.

Figure 3:
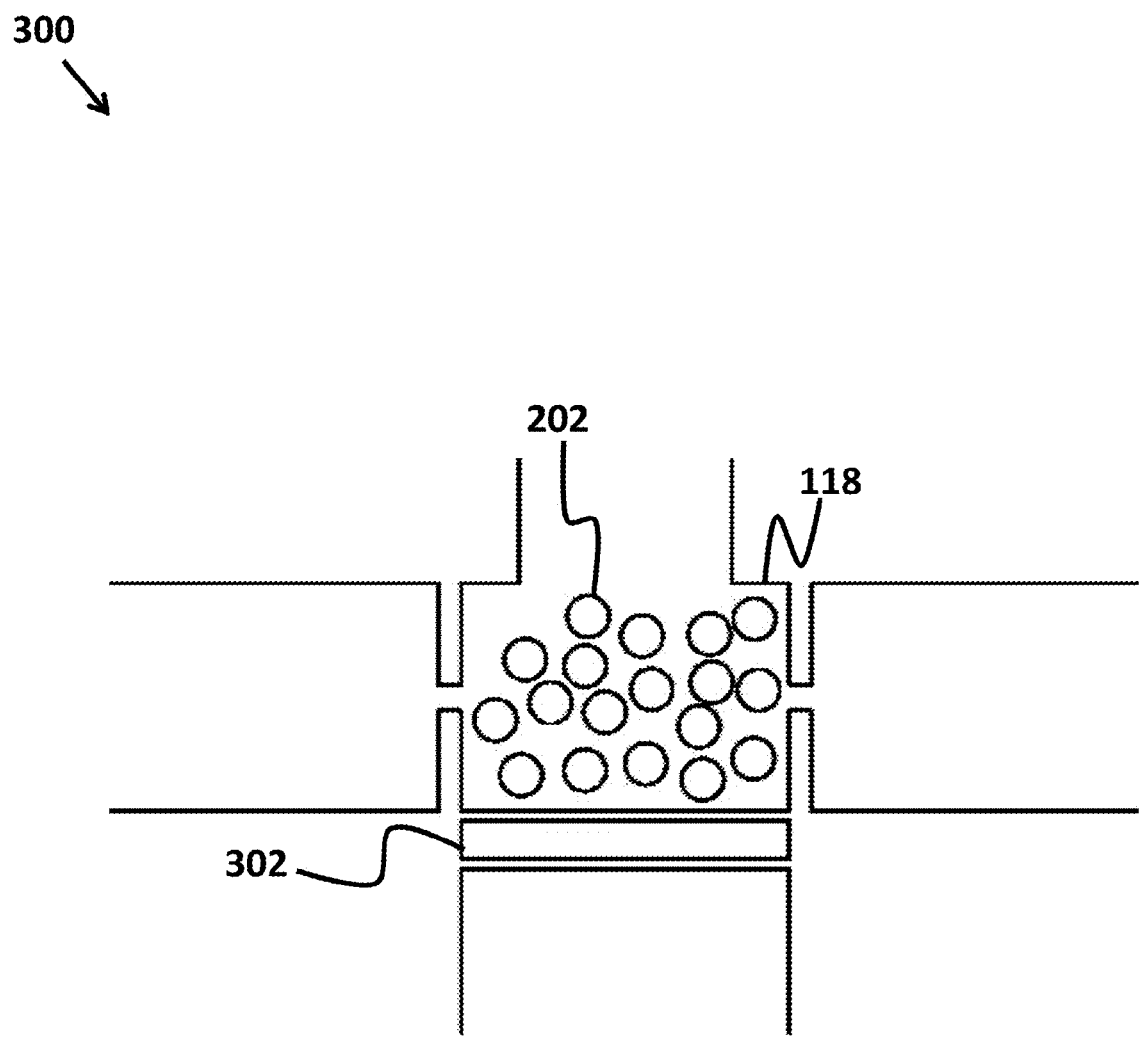
FIG. 3 shows a top view of a detection region with a liquid sieve at one end according to the present invention.

FIG. 3 shows an alternate embodiment 300 of the invention, where the detection region 118 includes a sieve material 302 that allows the carrying fluid to continue moving but stops the detection particles 202. For example, a molecular sieve will allow water to pass under pressure through atomic level openings in the material, but will block passage of larger particles.

Figure 4:
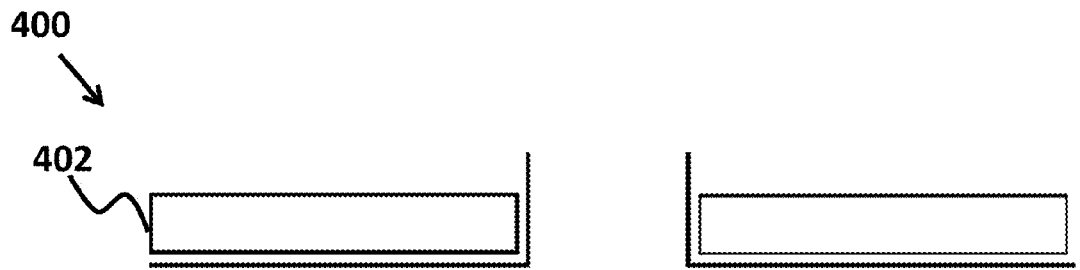
FIGS. 4a-4b show flexible microfluidic walls in an unconstructed state and in a constricted state according to the present invention.
Figure 4:
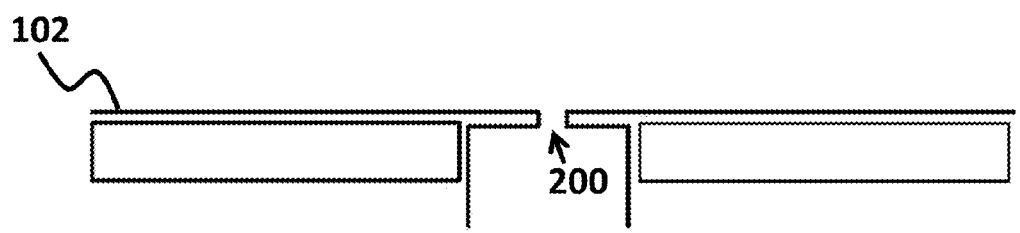
Figure 4:
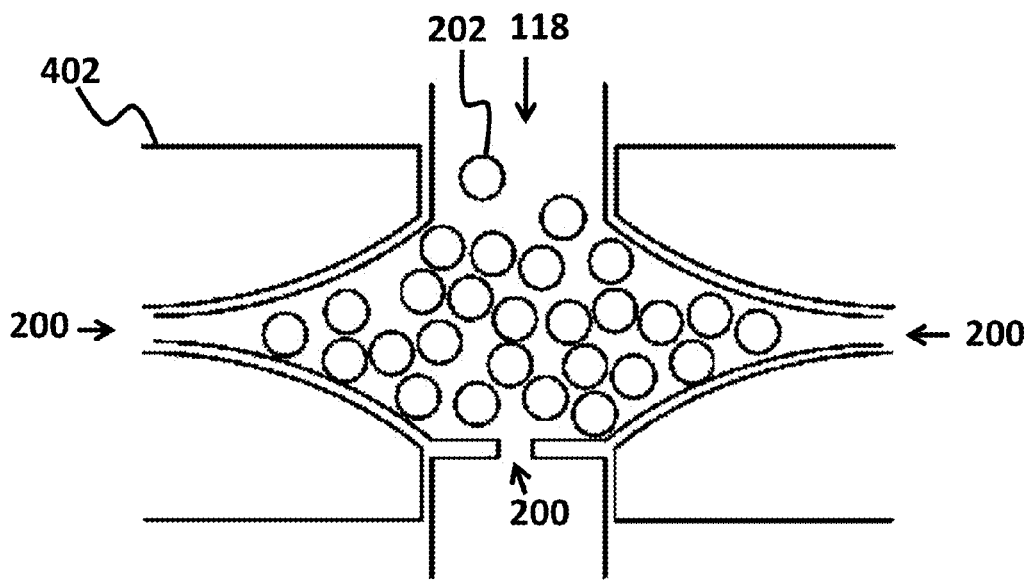

FIGS. 4a and 4b show another embodiment of the invention 400 that includes a reconfigurable detection region. According to the current embodiment 400 the main channel 102 can be constructed from a flexible material, such as silicone elastomers. If a bladder region 402 was placed in near proximity to the main channel 102, any pressure applied to the bladder 402 will expand into the main channel 102, and provide a constricting region 200 to the channel 102. This approach allows for detection regions 118 to be repeatedly created and released, thus allowing for repeated use with different detection particles. It also allows one generic design to use particles 202 of different sizes, as the channel can be configured for any size constriction.

Figure 5:
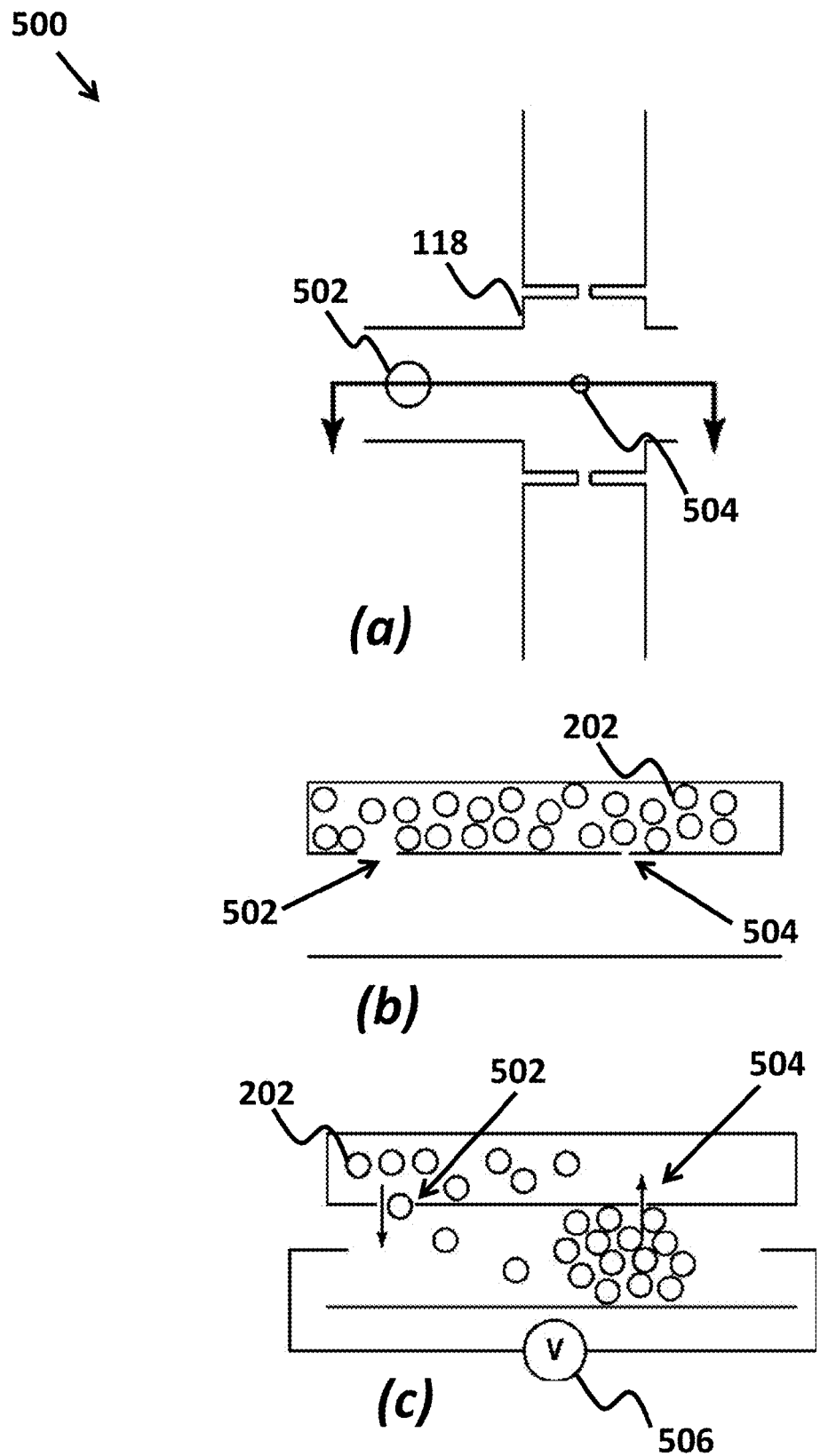
FIGS. 5a-5c show an alternative form of nanoparticle delivery according to the present invention.

FIGS. 5a-5c show a further embodiment 500 for supplying particles 202 to a detection region. FIG. 5a shows a top view of the current embodiment 500 that includes an annotation to indicate the centerline of the cutaway views in FIGS. 5b and 5c. According to the figures, a third dimension is considered. Here, the top surface of the detection region 118 contains a first aperture 502 that is large enough to pass particles 202 and a second aperture 504 that is smaller than the particles. When an electric potential 506 is applied along the detection region 118, the fluid and particles 202 will flow out of the first aperture 502 by electroosmosis. The fluid will flow back through the second aperture 504, but the particles 220 will not pass. This method creates local high density of particles 202 at the second aperture 504.

Figure 6:
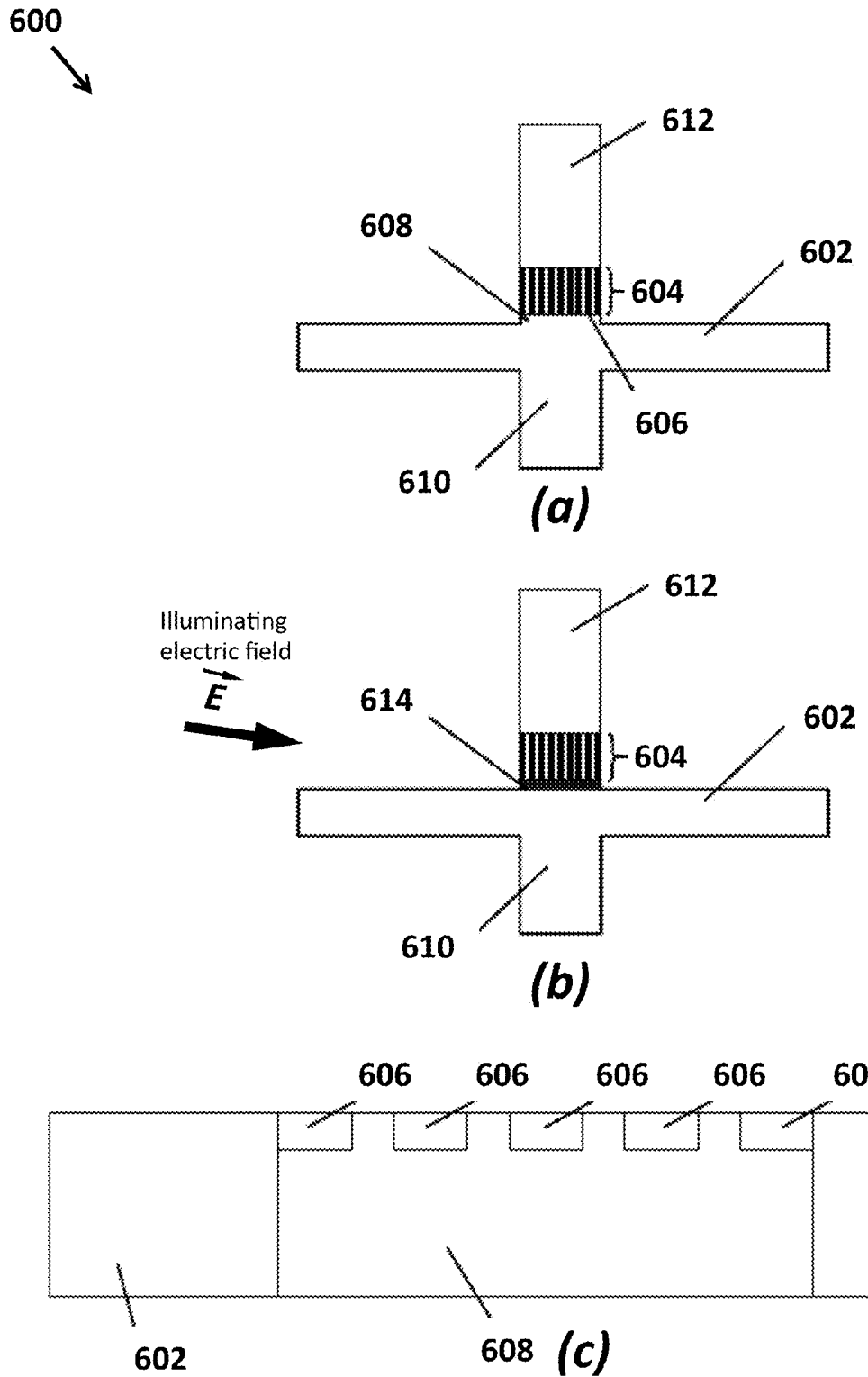
FIGS. 6a-6d show a microfluidic separation and detection device, according to one embodiment of the invention.
Figure 6:
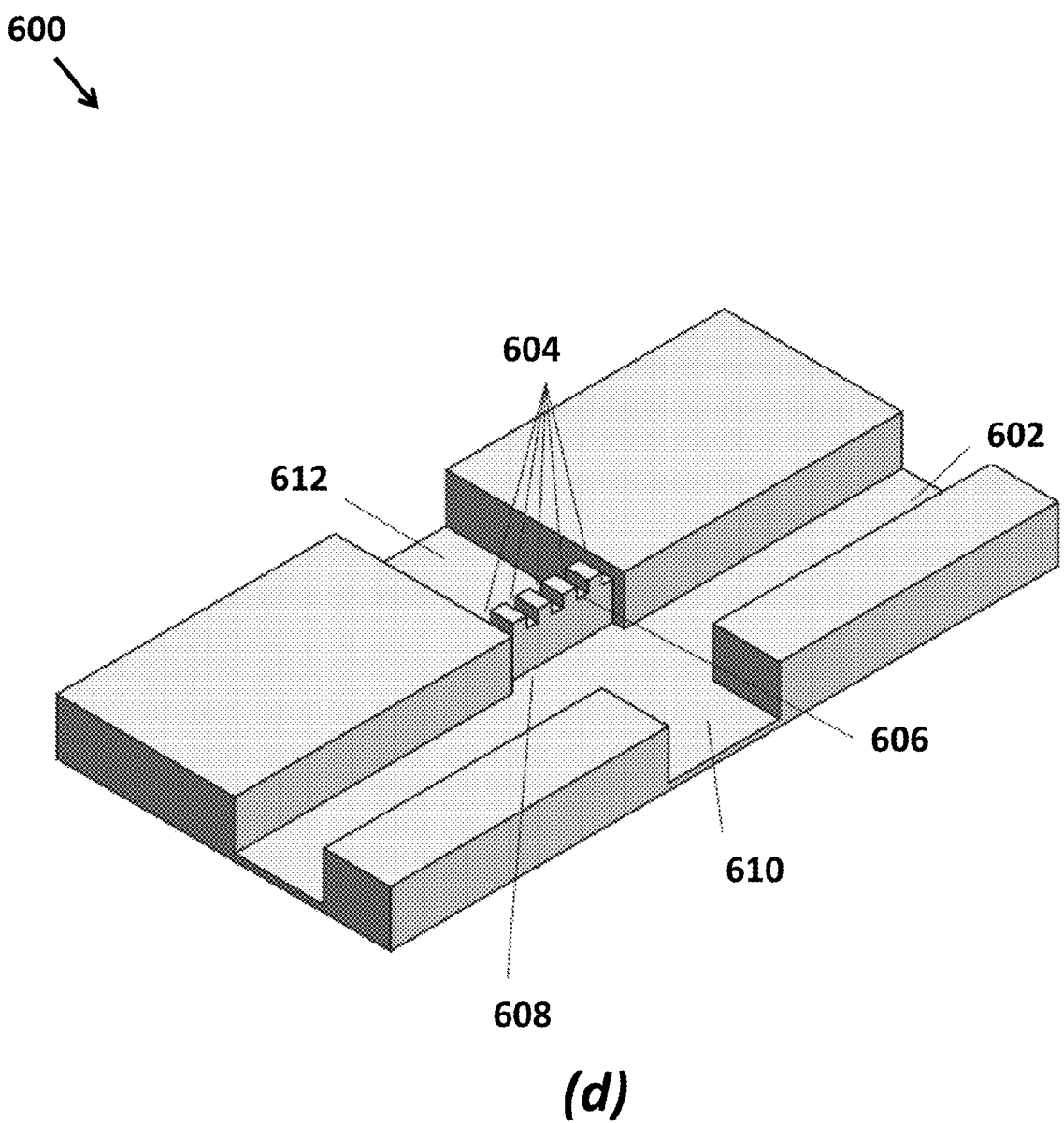

FIG. 6a shows a top view of one embodiment of the current invention that includes a microfluidic separation and detection device 600 having a second sample channel region 602, a first sample channel region 604 shown having an array of channels, a second detection region 606 at the planar interface of the first sample channel 604, a first detection region 608, a Raman-scattering nanoparticle loading channel 610, and a detection channel 612. The first sample channel region 604 and the second detection region 606 are connected, providing geometric constraints that prevent particles of a certain size from passing from the second sample channel 602 to the detection channel 612 and vice versa. FIG. 6b shows a top view of the microfluidic separation and detection device with loaded Raman-scattering nanoparticles 614 in the first detection region 608. FIG. 6c shows a cross-sectional view of the second and first detection regions 606 and 608, respectively, from the second sample channel region 602. At the planar interface of the second detection region 606 the second detection region 606 is smaller than the first detection region 608 and the second sample channel region 602 to trap particles larger than the second detection region 606 within the first detection region 608.

FIG. 6d shows an isometric projection view of a microfluidic separation and detection device 600 having a second sample channel region 602, a first sample channel region 604, a second detection region 606, a first detection region 608, a Raman-scattering nanoparticle loading channel 610 connected, and a detection channel 612. The first sample channel region 604 and the second detection region 606 are connected, providing geometric constraints that prevent particles of a certain size from continuing past the detection channel 612.

Figure 7:
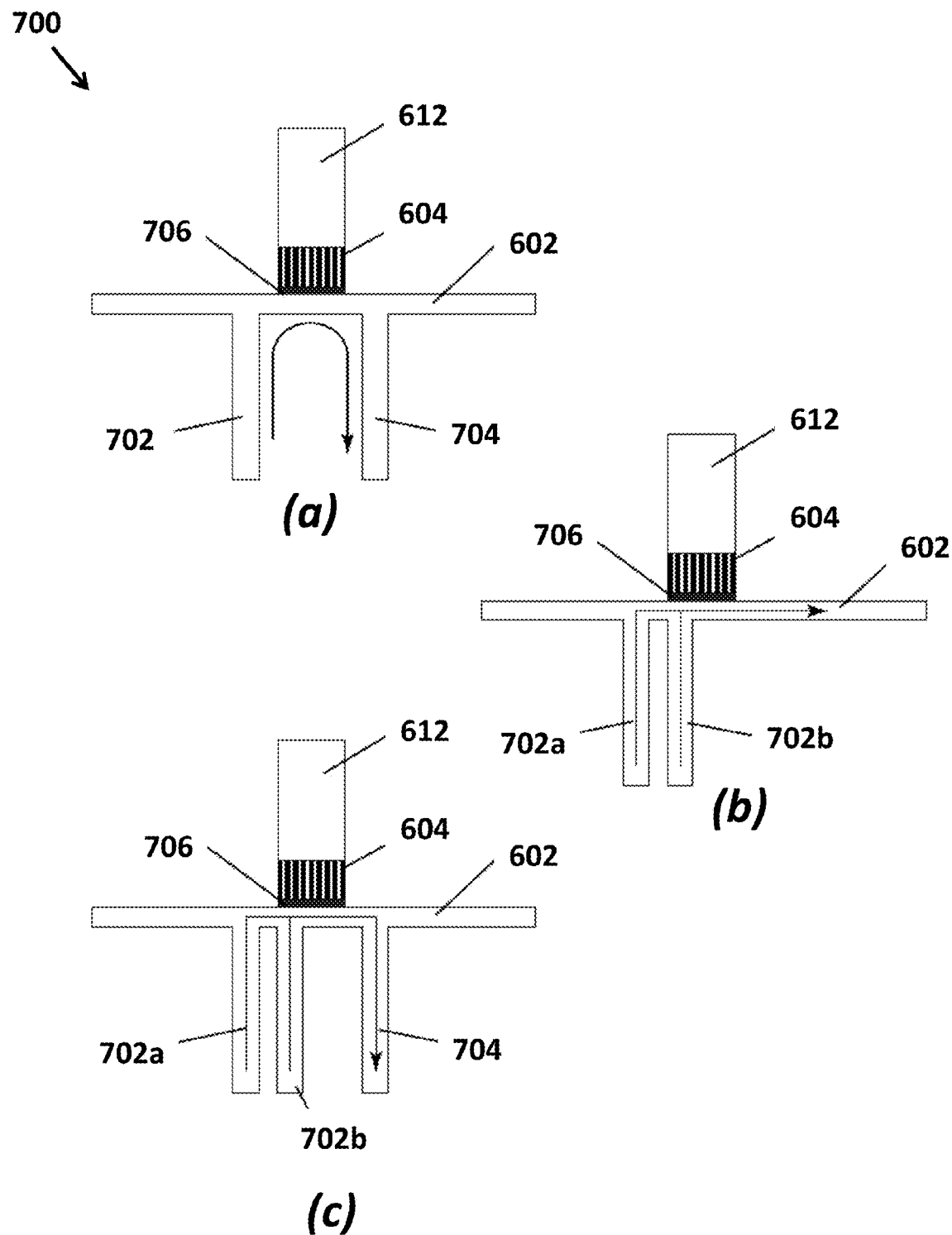
FIGS. 7a-7c show microfluidic separation and detection devices having different configurations of input channels and output channels, according to different embodiments of the current invention.

FIGS. 7a-7c shows further embodiments of a microfluidic separation and detection device 700, where the Raman-scattering nanoparticle loading channel (610 of FIGS. 6a-6d) is divided into multiple segments that include a Raman-scattering nanoparticle input channel 702 and a Raman-scattering nanoparticle output channel 704, as shown in FIG. 7a, on either side of the loaded (trapped) Raman-scattering nanoparticles 706 in the first detection region 608. This embodiment allows the particles to flow continuously to build a higher density, or to be washed by switching from a Raman-scattering nanoparticle solution to a cleaning solution.

According to another embodiment, FIG. 7b shows two Raman-scattering nanoparticle input channels 702a and 702b disposed on the same side of the loaded (trapped) Raman-scattering nanoparticles 706, with an output along the sample channel 602.

In a further embodiment, FIG. 7c shows two Raman-scattering nanoparticle input channels 702a and 702b disposed to enable multiple Raman-scattering nanoparticle types to be loaded simultaneously through an output channel 704.

Figure 8:
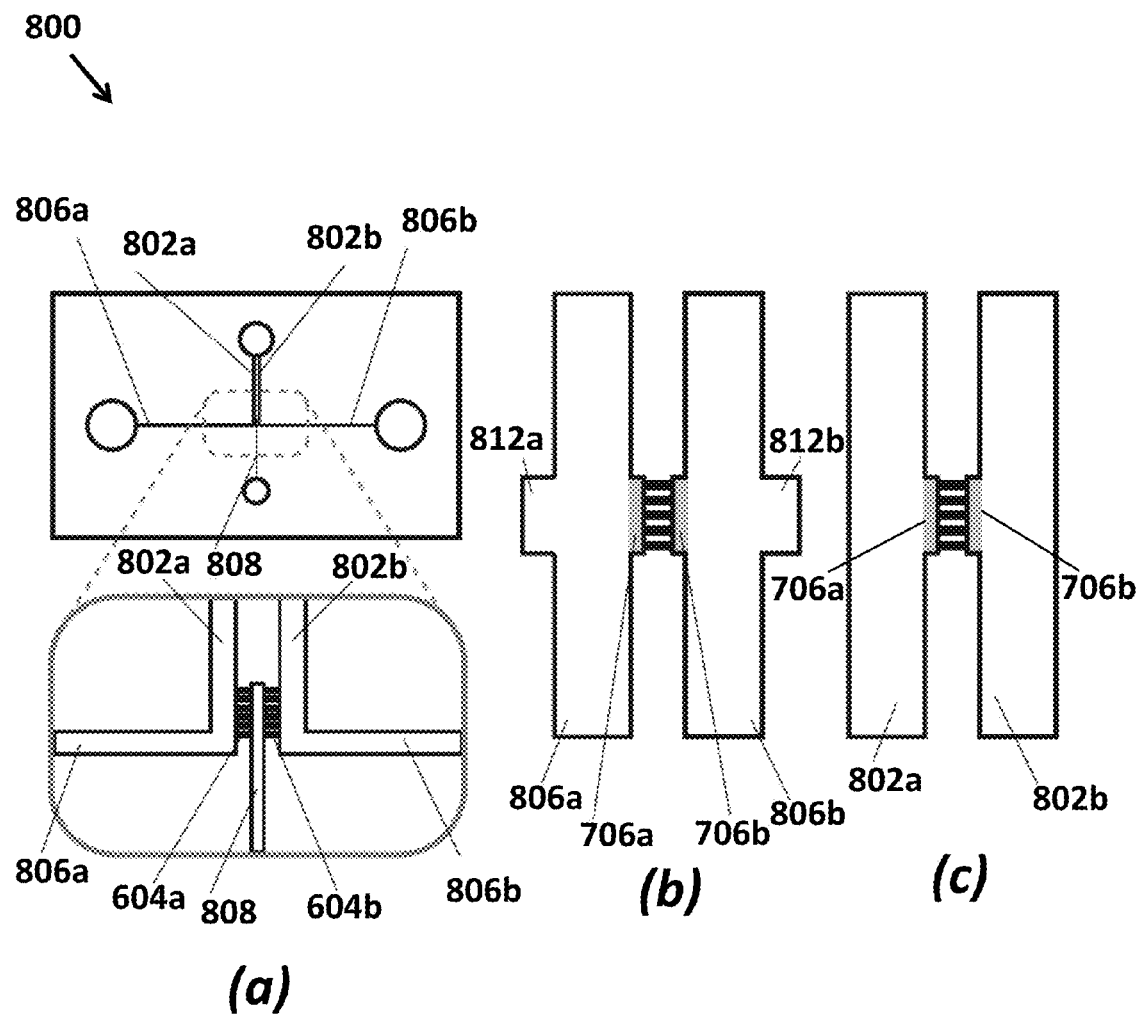
FIGS. 8a-8c show microfluidic separation and detection devices having different configurations of the detection regions and sample channels, according to different embodiments of the current invention.

FIGS. 8a-8c show additional embodiments of the invention, where two parallel sample channels 802a and 802b are connected through detection regions 604a and 604b and to lateral sample channels 806a and 806b, respectively, to a detection channel 808 as shown in FIG. 8a.

According to another embodiment shown in FIG. 8b, the loaded Raman-scattering nanoparticles 810a and 801b in each channel are show with Raman-scattering nanoparticle loading channels 812a and 812b connected to a single detection region 604.

In a further embodiment, the parallel sample channels 802a and 802b act as Raman-scattering nanoparticle loading channels connected to a single detection region 804, as shown in FIG. 8c.

Figure 9:
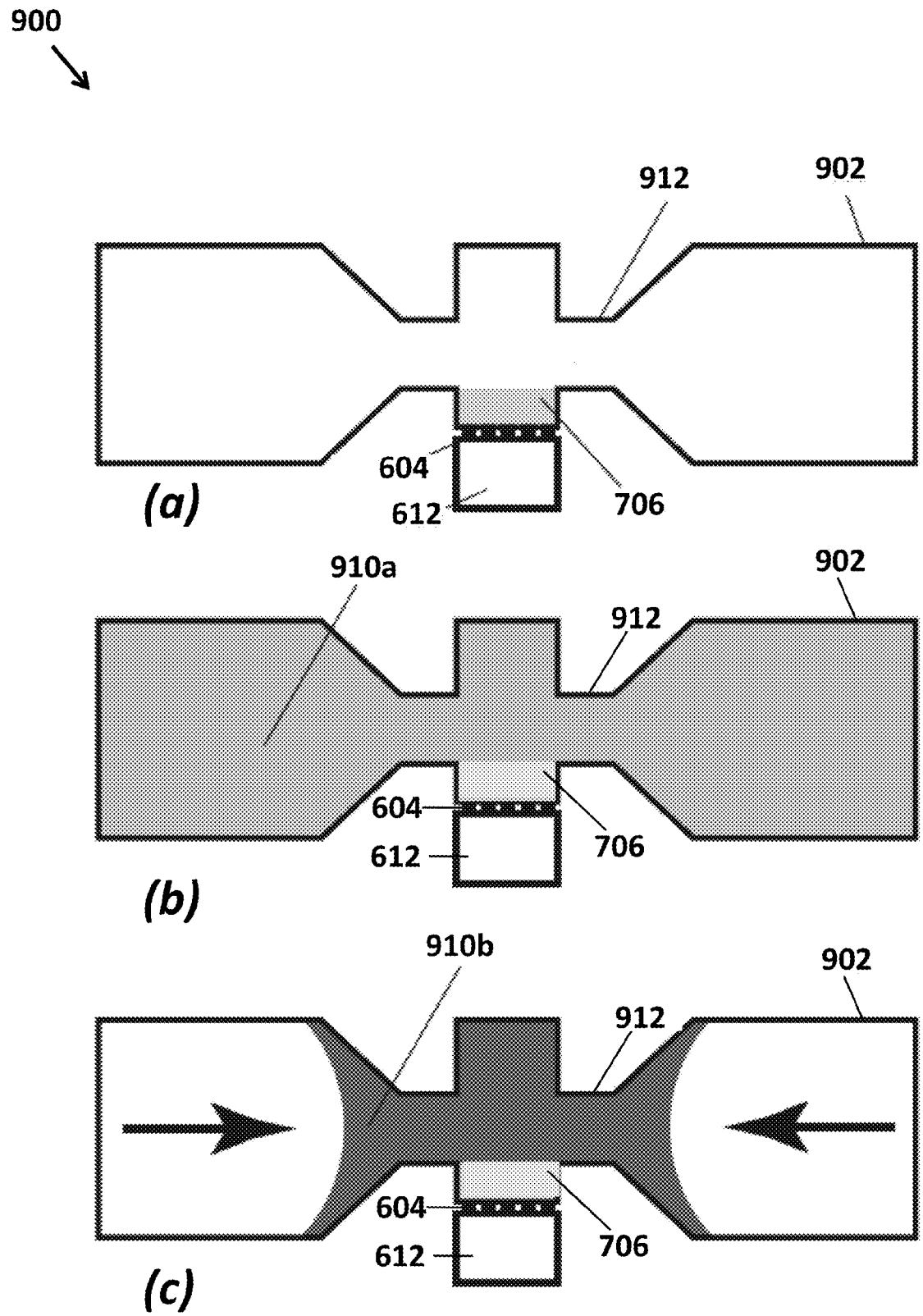
FIGS. 9a-9c show a microfluidic separation and detection device having a sample channel with a constricting region to concentrate the analyte, according to one embodiment of the invention.

FIGS. 9a-9c show a further embodiment 900 of the current invention, where shown is a sample channel 902, loaded Raman-scattering nanoparticles 706, a detection region 604, and a detection channel 804 (see FIG. 9a). When filled with the sample 910, such as analyte, as shown in FIG. 9b, a low analyte 910a concentration is in contact with the loaded Raman-scattering nanoparticles 904. As the solvent evaporates, shown in FIG. 9c, the low concentration analyte 904a will increase to a concentrated analyte 904b. The capillary forces from the constricted region 912 of the sample channel 902 will draw the concentrated analyte 910b in contact with the loaded Raman-scattering nanoparticles 706. The arrows indicate how the solution flows as analyte 910 evaporates.

Figure 10:
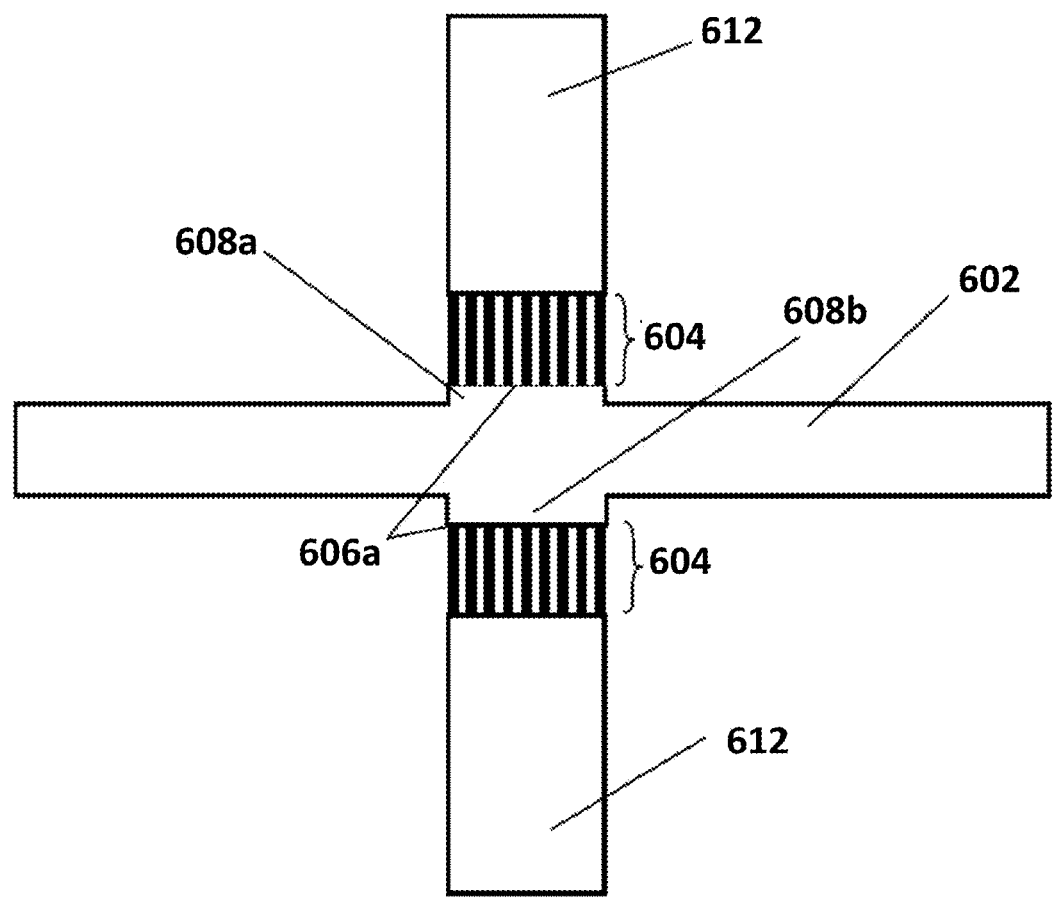
FIG. 10 shows microfluidic separation and detection device having detection regions disposed on opposing sides of a sample channel, according to one embodiment of the invention.

FIG. 10 shows a further embodiment of the microfluidic separation and detection device 1000 where shown is one sample channel 602 intersecting a detection channel 808 having two detection regions 604a/604b and two second sample channel regions 608a/608b inside and disposed on each side of the sample channel 602.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the device may be injection molded, constructed of elastomers, or processed using semiconductor methods and materials. The channels may contain curved segments to extend their lengths or may have varying depths to encourage separation. The detection particles could combine multiple signaling and binding mechanisms, such as being magnetic and fluorescent to enhance optical detection within a magnetic field. All such variations are considered to be within the scope and spirit of the present invention as defined by the following claims and their legal equivalents.

What is claimed is:

1. A microfluidic separation device comprising:
   a. a first sample channel region and a second sample channel region, wherein said first sample channel region comprises an array of channels that are smaller than said second channel region;
   b. a first detection region and a second detection region located at a planar interface of said first sample channel region;
   c. a detection channel;
   d. an illuminating electric field;
   e. Raman-scattering nanoparticles, wherein said Raman-scattering nanoparticles comprise surface plasmon resonances for detection when illuminated by said illuminating electric field, wherein said surface plasmon resonances create an enhanced local electric field along specific directions, wherein said enhanced local electric field results in an enhanced Raman response; and
   f. a Raman-scattering nanoparticle input channel disposed to input said Raman-scattering nanoparticles into said second sample channel region, wherein said Raman-scattering nanoparticles are larger than said cross-section of said first sample channel region and larger than said cross-section of said second detection region, wherein said Raman-scattering nanoparticles are disposed to collect in said first detection region to form region of densely packed said Raman-scattering nanoparticles.

2. The microfluidic separation device of claim 1 further comprises a Raman-scattering nanoparticle output channel, wherein said Raman-scattering nanoparticle input channel and said Raman-scattering nanoparticle output channel are disposed opposite said densely packed Raman-scattering nanoparticles along said second sample channel region, where said nanoparticle input channel is disposed at a proximal side of said densely packed Raman-scattering nanoparticles and said Raman-scattering nanoparticle output channel is disposed at a distal side of said densely packed Raman-scattering nanoparticles.

3. The microfluidic separation device of claim 1 further comprises said first Raman-scattering nanoparticle input channel and a second said Raman-scattering nanoparticle input channel, wherein said first and said second Raman-scattering nanoparticle input channels are disposed proximal to and parallel each other.

4. The microfluidic separation device of claim 1 further comprises a Raman-scattering nanoparticle output channel, said first Raman-scattering nanoparticle input channel and a second said Raman-scattering nanoparticle input channel, wherein said first and said second Raman-scattering nanoparticle input channels disposed proximal to and parallel with each other, wherein said second Raman-scattering nanoparticle input channel and said Raman-scattering output channel are disposed opposite said densely packed Raman-scattering nanoparticles along said second sample channel region, where said nanoparticle input channel is disposed at a proximal side of said densely packed Raman-scattering nanoparticles and said Raman-scattering nanoparticle output channel is disposed at a distal side of said densely packed Raman-scattering nanoparticles.

5. The microfluidic separation device of claim 1, wherein a first said detection region and a second said detection region are dispose on opposite sides of said detection channel, wherein a first said sample channel is connected to said first detection region and a second said sample channel is connected to said second detection region, wherein said first sample channel is parallel with said second sample channel.

6. The microfluidic separation device of claim 1, wherein a first said sample channel is connected to a proximal side of said detection region and a second said sample channel is connected a distal side of said detection region, wherein said densely packed Raman-scattering nanoparticles are disposed on opposite sides of said detection region.

7. The microfluidic separation device of claim 1, wherein a first said sample channel having a first said Raman-scattering nanoparticle loading channel is connected to a proximal side of said detection region and a second said sample channel having a second said Raman-scattering nanoparticle loading channel is connected a distal side of said detection region, wherein said densely packed Raman-scattering nanoparticles are disposed on opposite sides of said detection region.

8. The microfluidic separation device of claim 1, wherein said sample channel comprises a first constricted region and a second constricted region disposed on opposite sides of said detection region.

9. The microfluidic separation device of claim 1, wherein a first said detection region is disposed on a first side of said sample channel and a second said detection region is disposed on a second side of said sample channel, wherein said first and said second detection regions are opposite of each other across said sample channel.

* * * * *